United States Patent
Winner

(10) Patent No.: US 9,326,467 B1
(45) Date of Patent: May 3, 2016

(54) *TAGETES PATULA* VARIETY 'PAS1077390'

(71) Applicant: Ball Horticultural Company, West Chicago, IL (US)

(72) Inventor: Blair L. Winner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 14/552,371

(22) Filed: Nov. 24, 2014

(51) Int. Cl.
*A01H 5/02* (2006.01)

(52) U.S. Cl.
CPC ........................................ *A01H 5/02* (2013.01)

(58) Field of Classification Search
None
See application file for complete search history.

(56) References Cited

PUBLICATIONS

Howe et al 1997, Proc. Florida State Hort. Soc. 110: 350-357.*
U.S. Appl. No. 14/552,354, filed Nov. 24, 2014, Winner.
U.S. Appl. No. 14/552,357, filed Nov. 24, 2014, Winner.
U.S. Appl. No. 14/552,361, filed Nov. 24, 2014, Winner.
U.S. Appl. No. 14/552,368, filed Nov. 24, 2014, Winner.
U.S. Appl. No. 14/552,377, filed Nov. 24, 2014, Winner.
Liberty Hyde Bailey Hortorium, Hortus Third, Macmillan Publishing Company, 1976.
Ball RedBook, 16th ed., Ball Publishing, 1998.
Little Devil Fire French Marigold Plant Information, available at <http://www.ballseed.com/growers/plant_info.aspx?phid=040800839001840>, accessed Jun. 16, 2015.
Janie Deep Orange Marigold Plant Information, available at <http://parkseed.com/janie-deep-orange-marigold-seeds/p/01266-PK-P1/>, accessed Jun. 16, 2015.

* cited by examiner

*Primary Examiner* — David H Kruse
(74) *Attorney, Agent, or Firm* — Dentons US LLP

(57) ABSTRACT

The invention provides seed and plants of *Tagetes patula* variety 'PAS1077390'. The invention thus relates to the plants, seeds, and tissue cultures of *Tagetes patula* variety 'PAS1077390', and to methods for producing a marigold plant produced by crossing such plants with themselves or with another marigold plant, such as a plant of another genotype. The invention further relates to seeds and plants produced by such crossing. The invention further relates to parts of such plants, including the gametes of such plants.

22 Claims, 2 Drawing Sheets

7568-2-1-6
↓ ⊗
7568-2-1-6-06
↓ ⊗
7568-2-1-6-06-m(100)   yr 2011

'PAS1077390'

FIG. 1 (Continued)

TAGETES PATULA VARIETY 'PAS1077390'

FIELD OF THE INVENTION

The present invention relates to the field of plant breeding and, more specifically, to *Tagetes patula* plants and related methods and compositions for the production thereof.

BACKGROUND OF THE INVENTION

The *Tagetes* genus is a member of the family Asteraceae, alternatively known as Compositae, and comprises around thirty species of strongly scented annual or perennial herbs. *Tagetes* are native from Arizona and New Mexico to Argentina. Cultivated genera include *Tagetes erecta*, commonly referred to as African marigold, *Tagetes patula*, French marigold, *Tagetes erecta* x *patula*, also known as triploid marigolds, and *Tagetes tenuifolia*, also known as *Tagetes signata* or commonly signet marigold.

Cultivated marigolds perform well in dry or moist conditions with strongly scented, showy flowers that are excellent in borders and as cut flowers. They produce a long-term display of colors, which include yellow, orange, and gold, with shades of red and maroon from the triploid and French types. Flowers range in size from 2.5 cm for the French varieties to as broad a 13 cm for some of the African varieties. Plants range from 15 to 91 cm in height and fill in well in the garden. Of the cultivated marigolds, the French marigolds are especially valued in the landscape as a colorful upright-mounding border plant. Under high humidity and high night temperatures, French marigolds typically stretch and exhibit reduced flowering.

SUMMARY OF THE INVENTION

In one aspect, the present invention provides a *Tagetes patula* plant of the variety designated 'PAS1077390'. Also provided are *Tagetes* plants having all the physiological and morphological characteristics of *Tagetes patula* variety 'PAS1077390'. Parts of the *Tagetes* plant of the present invention are also provided, for example, including a flower, pollen, a leaf, an ovule, and a cell of the plant.

The invention also concerns seed of *Tagetes patula* variety 'PAS1077390'. The *Tagetes* seed of the invention may be provided, in certain illustrative embodiments, as an essentially homogeneous population of *Tagetes* seed of the variety designated 'PAS1077390'. Essentially homogeneous populations of seed are generally free from substantial numbers of other seed. Therefore, in one embodiment, seed of variety 'PAS1077390' may be defined as forming at least about 90% of the total seed, including at least about 91%, 92%, 93%, 94%, 95%, 96%, 97%, 98%, 99%, or more of the seed. The population of *Tagetes* seed may be particularly defined as being essentially free from hybrid seed. The seed population may be separately grown to provide an essentially homogeneous population of *Tagetes* plants designated variety 'PAS1077390'.

In another aspect of the invention, a plant of *Tagetes patula* variety 'PAS1077390' comprising an added heritable trait is provided. The heritable trait may comprise a genetic locus that is, for example, a dominant or recessive allele. In one embodiment of the invention, a plant of *Tagetes patula* variety 'PAS1077390' is defined as comprising a single locus conversion. In specific embodiments of the invention, an added genetic locus confers one or more traits such as, for example, herbicide tolerance, drought or heat tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of variety 'PAS1077390' is provided. The tissue culture will preferably be capable of regenerating plants capable of expressing all of the physiological and morphological characteristics of the variety, and of regenerating plants having substantially the same genotype as other plants of the variety. Examples of some of the physiological and morphological characteristics of variety 'PAS1077390' include those traits set forth in the tables herein. The regenerable cells in such tissue cultures may be derived, for example, from embryos, meristems, cotyledons, pollen, leaves, anthers, roots, root tips, pistils, flowers, cuttings, seeds, and stems. Still further, the present invention provides *Tagetes* plants regenerated from a tissue culture of the invention, the plants having all the physiological and morphological characteristics of variety 'PAS1077390'.

In yet another aspect of the invention, processes are provided for producing *Tagetes* seeds and plants, which processes generally comprise crossing a first parent *Tagetes* plant with a second parent *Tagetes* plant, wherein at least one of the first or second parent *Tagetes* plants is a plant of the variety designated variety 'PAS1077390'. These processes may be further exemplified as processes for preparing hybrid *Tagetes* seed or plants, wherein a first *Tagetes* plant is crossed with a second *Tagetes* plant of a different, distinct variety to provide a hybrid that has, as one of its parents, the *Tagetes* variety 'PAS1077390'. *Tagetes patula* variety 'PAS1077390' may be used as either the female or the male parent in such crosses. In these processes, crossing will result in the production of seed. The seed production occurs regardless of whether the seed is collected or not. In a specific embodiment, *Tagetes* variety 'PAS1077390' may be used as a male parent in a cross with another variety such as *Tagetes erecta* to produce triploid seed, which may produce sterile triploid plants.

In one embodiment of the invention, the first step in "crossing" comprises planting seeds of a first and second parent *Tagetes* plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent *Tagetes* plants into plants that bear flowers. A third step may comprise preventing self-pollination of the plants, such as by emasculating the flowers, (i.e., killing or removing pollen).

A fourth step for a hybrid cross may comprise cross-pollination between the first and second parent *Tagetes* plants. Yet another step comprises harvesting the seeds from at least one of the parent *Tagetes* plants. The harvested seed can be grown to produce a *Tagetes* plant such as a hybrid *Tagetes* plant.

In an embodiment, a plant of the invention may be crossed with a plant of *Tagetes patula* variety 'Little Devil Fire' as the second *Tagetes* plant.

The present invention also provides the *Tagetes* seeds and plants produced by a process that comprises crossing a first parent *Tagetes* plant with a second parent *Tagetes* plant, wherein at least one of the first or second parent *Tagetes* plants is a plant of the variety designated 'PAS1077390'. In one embodiment of the invention, *Tagetes* seed and plants produced by the process are first generation (F1) hybrid *Tagetes* seed and plants produced by crossing a plant in accordance with the invention with another, distinct plant. The present invention further contemplates plant parts of such an F1 hybrid *Tagetes* plant, and methods of use thereof. Therefore, certain exemplary embodiments of the invention provide an F1 hybrid *Tagetes* plant and seed thereof.

In still yet another aspect of the invention, the genetic complement of the *Tagetes* variety designated 'PAS1077390' is provided. The invention thus provides *Tagetes* plant cells that have a genetic complement in accordance with the *Tagetes* plant cells disclosed herein, and plants, seeds, and plant parts containing such cells. Plant genetic complements may be assessed by genetic marker profiles, and by the expression of phenotypic traits that are characteristic of the expression of the genetic complement.

In still yet another aspect, the present invention provides hybrid genetic complements, as represented by *Tagetes* plant cells, tissues, plants, and seeds, formed by the combination of a haploid genetic complement of a *Tagetes* plant of the invention with a haploid genetic complement of a second *Tagetes* plant, preferably another, distinct *Tagetes* plant. In another aspect, the present invention provides a *Tagetes* plant regenerated from a tissue culture that comprises a hybrid genetic complement of this invention.

In still yet another aspect, the invention provides a method of determining the genotype of a plant of *Tagetes patula* variety 'PAS1077390' comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from variety 'PAS1077390', the method comprising the steps of: (a) preparing a progeny plant derived from variety 'PAS1077390', wherein said preparing comprises crossing a plant of the variety 'PAS1077390' with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from variety 'PAS1077390'. The plant derived from variety 'PAS1077390' may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from variety 'PAS1077390' is obtained which possesses some of the desirable traits of the variety as well as potentially other selected traits.

In still yet another aspect, the invention provides a method of producing a *Tagetes patula* plant variety comprising the steps of: (a) crossing a plant of *Tagetes patula* variety 'Little Devil Fire' with a second *Tagetes patula* plant to produce progeny; and (b) backcrossing for at least about 1 to 7 subsequent generations a plant of *Tagetes patula* variety 'Little Devil Fire' to said progeny; wherein said backcrossing comprises selecting a progeny plant comprising the traits of *Tagetes patula* plant variety 'PAS1077390'.

These and other features and advantages of this invention are described in, or are apparent from, the following detailed description of various exemplary embodiments of the devices and methods according to this invention.

DETAILED DESCRIPTION OF THE INVENTION

Figure 1:
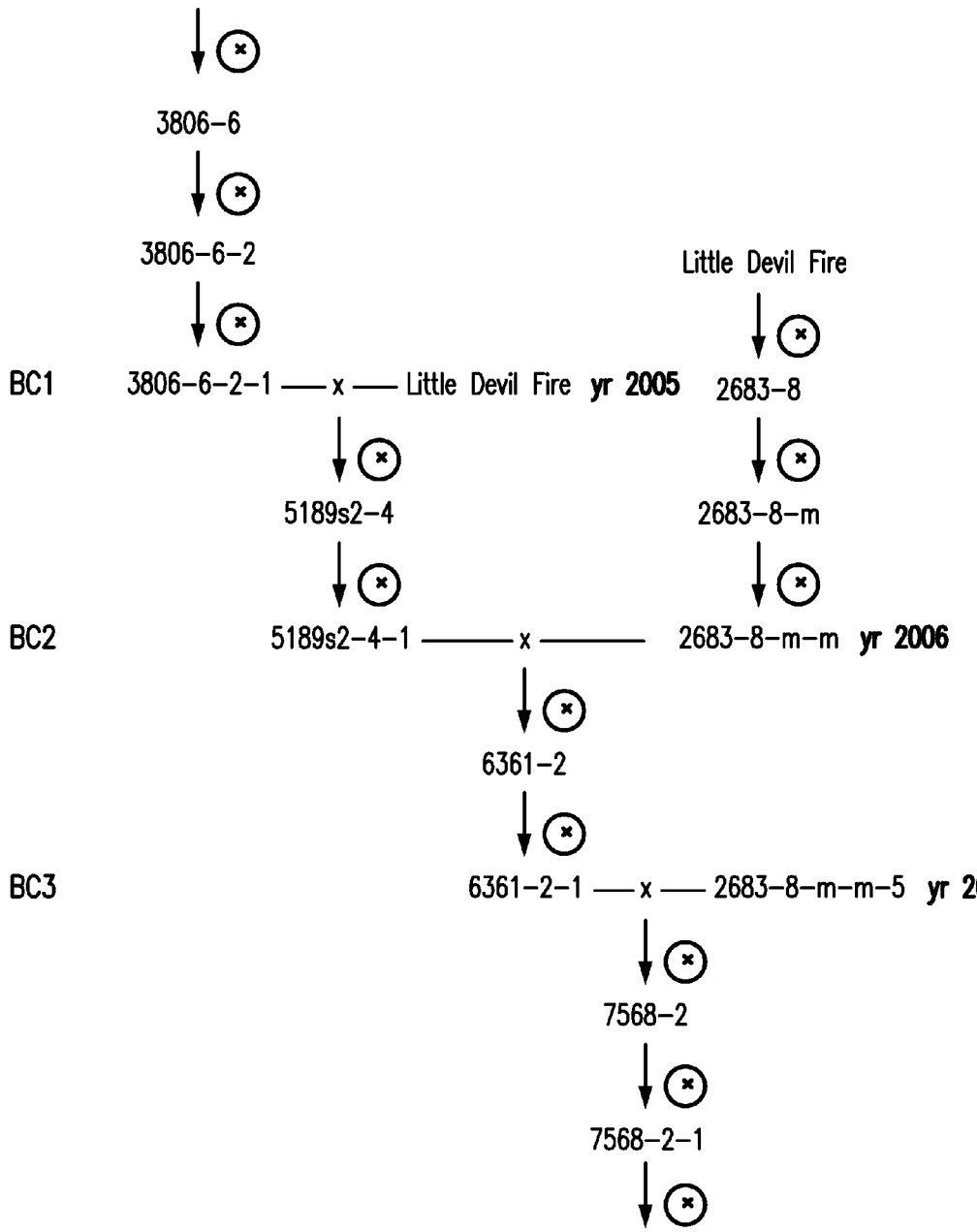
FIG. 1: Shows the crossing and selections that led directly to *Tagetes patula* variety 'PAS1077390'.

The invention provides methods and compositions relating to plants, seeds, and derivatives of *Tagetes patula* variety 'PAS1077390'. Variety 'PAS1077390' has not been observed under all possible environmental conditions to date. Accordingly, it is possible that the phenotype may vary somewhat with variations in the environment, such as temperature, light intensity, and day length, without, however, any variance in genotype. The variety of the present invention is one of a series of colors that continue to flower and maintain a compact habit under high humidity and high night temperatures.

The following descriptions and measurements describe plants produced from seed and grown under conditions comparable to those used in commercial practice. The plants were grown utilizing a soilless growth medium in trays having 2⅜"×2⅜" growing cells in a greenhouse in Elburn, Ill. Greenhouse temperatures were maintained at approximately 72° F. to 86° F. (22.2° C. to 30° C.) during the day and approximately 61° F. to 69° F. (16.1° C. to 20.6° C.) during the night. No supplemental lighting was provided. After seven weeks, plants were transferred to one-gallon containers and grown outdoors in Elburn, Ill. for six weeks. Measurements and numerical values represent averages of typical plants.

The chart used in the identification of colors described herein is The R.H.S. Colour Chart of The Royal Horticultural Society, London, England, 2007 edition, except where general color terms of ordinary significance are used. The color values were determined in June 2014 under natural light conditions in Elburn, Ill.

A. Origin and Breeding History of *Tagetes Patula* Variety 'PAS1077390'

The crossing and selections that led to *Tagetes patula* variety 'PAS1077390' are shown in FIG. 1. *Tagetes patula* variety 'PAS1077390' is uniform and stable. A small percentage of variants can occur within commercially acceptable limits for almost any characteristic during the course of repeated multiplication. However, no variants are expected.

B. Physiological and Morphological Characteristics of *Tagetes Patula* Variety 'PAS1077390'

In accordance with one aspect of the present invention, there is provided a plant having the physiological and morphological characteristics of *Tagetes patula* 'PAS1077390'. A description of the physiological and morphological characteristics of *Tagetes patula* variety 'PAS1077390' is presented in Table 1.

TABLE 1

Physiological and Morphological Characteristics of *Tagetes patula* variety 'PAS1077390'

| | 'PAS1077390' | 'Little Devil Fire' |
|---|---|---|
| 1. OVERALL PLANT HABIT (at Flowering Stage): Data Collection Site: Elburn, Illinois, June 2014 | | |
| Species Type: 1 = *T. erecta* (African); 2 = *T. patula* (French); | 2 | 2 |

TABLE 1-continued

Physiological and Morphological Characteristics of
*Tagetes patula* variety 'PAS1077390'

| | 'PAS1077390' | 'Little Devil Fire' |
|---|---|---|
| 1. OVERALL PLANT HABIT (at Flowering Stage): Data Collection Site: Elburn, Illinois, June 2014 | | |
| 3 = *T. tenuifolia* (Signata); 4 = *T. lucida* (Sweet); 5 = Other Ploidy: 1 = Haploid; 2 = Diploid; 3 = Triploid; 4 = Tetraploid | 4 | 4 |
| Chromosome Number (1N) | 48 | 48 |
| Days from Planting to First Flowering | 35 to 40 | 35 to 40 |
| Flowering Season | Long season | Long season |
| Plant Height at Maturity (cm) | 15.0 | 13.1 |
| Plant Width at Maturity (cm) | 20.7 | 19.2 |
| Plant Height Class: 1 = Extra Dwarf <20 cm; 2 = Dwarf 25-35 cm; 3 = Semi-dwarf; 4 = Tall | 1 | 1 |
| Plant Width Class: 1 = Compact; 2 = Semi-compact; 3 = Spreading/Lax | 1 | 1 |
| Growth Form: 1 = Upright; 2 = Semi-prostrate; 3 = Prostrate | 1 | 1 |
| 2. FOLIAGE: | | |
| Leaf Type: 1 = Simple (pseudo-compound); 2 = Compound | 1 | 1 |
| Leaf Shape: 1 = Filiform; 2 = Lanceolate; 3 = Elliptic; 4 = Obovate; 5 = Ovate | 3 | 3 |
| Leaf Margin: 1 = Entire; 2 = Crenate; 3 = Senate; 4 = Dentate; 5 = Incised; 6 = Other: Incised with serrate lobes | 6 | 6 |
| Leaf Width (mm) | 52 | 43 |
| Leaf Length (mm) | 74 | 84 |
| Leaf Color: 1 = Light Green; 2 = Medium Green; 3 = Dark Green; 4 = Bronze | 3 | 3 |
| RHS Colour Chart Code | N137A | N137A |
| Petiole Anthocyanin: 1 = Absent; 2 = Mild; 3 = Strong | 1 | 1 |
| Glands: 1 = Absent; 2 = Punctuate; 3 = Large Dots | 2 | 2 |
| Glands Location: 1 = Basal; 2 = Apical; 3 = Both | 1 | 1 |
| Leaf Odor: 1 = None; 2 = Mild Fragrance; 3 = Strong Fragrance; 4 = Mild "Marigold"; 5 = Strong "Marigold" | 4 | 4 |
| 3. STEM: | | |
| Profile: 1 = Straight; 2 = Zig Zag | 2 | 2 |
| Structure: 1 = Brittle; 2 = Intermediate; 3 = Flexible | 2 | 2 |
| Stem Anthocyanin: 1 = Absent; 2 = Along Veins Only; 3 = Solid Coloration below the first node | 3 | 3 |
| Stem Length from Base of Stem to Involucre of Terminal Flower (cm) | 5.5 | 5.0 |
| Stem Length from Base of Stem to Axil of Top Branch (cm) | 3.2 | 3.5 |
| Stem Length from Axil of Top Branch to Involucre of Terminal Flower (cm) | 2.3 | 1.5 |
| Number of Internodes Below First Branch | 1 | 1 |
| Number of First Order Branches | 4 | 4 |
| 4. FLOWER HEAD: | | |
| Type: 1 = Carnation; 2 = Chrysanthemum; 3 = Crested | 3 | 3 |
| Fullness: 1 = Single; 2 = Semi-double; 3 = Double | 3 | 3 |
| Silhouette: 1 = Flattened; 2 = Rosette; 3 = Globular | 3 | 3 |
| Number Flower Heads per Plant | 12 | 12 |
| Flower Head Diameter (mm) | 43 | 40 |
| Flower Odor: 1 = None; 2 = Mild Fragrance; 3 = Strong Fragrance; 4 = Mild "Marigold"; 5 = Strong "Marigold" | 4 | 4 |
| Flower Head Colors: 1 = Single; 2 = Bicolor; 3 = Tricolor | 1 | 3 |
| 5. FLOWER COLORS: | | |
| Ray Floret Color (RHS Colour Chart Code) | Orange N25C | Mahogany 185A with a thick margin of yellow 12A |
| Disk Floret Color (RHS Colour Chart Code) | Orange N25B with tips of orange N25C | Yellow-orange 21B with tips of yellow 12A |
| 6. RAY FLORET: | | |
| Length, Outer Row of First Matured Flower (mm) | 27 | 24 |
| Width, Outer Row of First Matured Flower (mm) | 15 | 17 |
| Shape: 1 = Flattened; 2 = Curled/Twisted ('Fantastic'); 3 = Slightly wavy | 3 | 3 |
| Apices: 1 = Entire; 2 = Lobed; 3 = Notched | 3 | 3 |
| Dorsal Surface: 1 = Glabrous; 2 = Pubescent; 3 = Pubescent on Apices Only | 1 | 1 |
| Ventral Surface: 1 = Glabrous; 2 = Pubescent; 3 = Pubescent on Apices Only | 1 | 1 |
| Dorsal Luster: 1 = Shiny; 2 = Dull | 2 | 2 |
| Ventral Luster: 1 = Shiny; 2 = Dull | 2 | 2 |
| Dorsal Color Pattern: 1 = Solid; 2 = Spotted; 3 = Striped; 4 = Picotee; 5 = Other | 1 | 4 |
| Ventral Color Pattern: 1 = Solid; 2 = Spotted; 3 = Striped; 4 = Picotee; 5 = Other | 1 | 1 |
| RHS Colour Chart Code | N25D | 13B |
| 7. DISC FLORETS: | | |
| Disc Flowers: 1 = Absent; 2 = Present but Covered; 3 = Present and Uncovered | 3 | 3 |
| Disc Flower Type: 1 = Not Quilled; 2 = Quilled | 1 | 1 |
| 8. SEEDS: Mature (Dry) Seeds | | |
| Seed Set: 1 = None; 2 = Poor; 3 = Fair; 4 = Good; 5 = Excellent | 4 | 4 |
| Seed Coat Color: 1 = White; 2 = Tan; 3 = Brown; 4 = Black; 5 = Other | 4 | 4 |
| Pappus Color: 1 = White; 2 = Tan; 3 = Brown; 4 = Other | 2 | 2 |
| Seeds per gram | 320 | 300 |

*These are typical values. Values may vary due to environment. Other values that are substantially equivalent are also within the scope of the invention.

C. Response of *Tagetes Patula* Variety 'PAS1077390' to High Humidity and High Night Temperatures To determine the effect of high night temperature and high humidity on plant habit and flowering, plants were grown in Ruskin, Fla. Seed was sown on Jun. 20, 2014 and for eleven days after germination, plants were maintained in a greenhouse with high temperatures ranging from approximately 86° F. to 88° F. (30° C. to 31° C.) and with a low temperature that was not colder than 75° F. (24° C.). The overall average temperature was 80° F. (27° C.). Plants were maintained outdoors after being transplanted in trays having 2⅜"×2⅜" growing cells and a soilless growth medium. After three weeks, plants were transplanted in the field. During the outdoor growth period, daily high temperatures ranged from approximately 81° F. to 97° F. (27° C. to 36° C.), daily low temperatures ranged from approximately 72° F. to 81° F. (22° C. to 27° C.), and the overall average temperature was 84° F. (29° C.). Humidity percentages for this period ranged from an average daily high of 99% to an average daily low of 60%, with an overall average of 82%. Outdoor temperature and humidity values are from the Tampa Airport weather station. Data was collected for ten plants of each variety six weeks after transplant to the field.

In comparison, the plants from the Elburn, Ill. trial were grown in one-gallon containers under an outdoor growth period having daily high temperatures ranging from approximately 65° F. to 90° F. (18° C. to 32° C.), daily low temperatures ranging from approximately 42° F. to 73° F. (6° C. to 23° C.), and an overall average temperature of 70° F. (21° C.). Humidity percentages for this period ranged from an average daily high of 89% to an average daily low of 45%, with an overall average of 67%. Outdoor temperature and humidity values are from the Aurora Airport weather station. Data was collected for ten plants of each variety six weeks after transplant outdoors.

A well-known commercial variety 'Bonanza Yellow' was used to illustrate the effect on flowering under the high night temperatures and high humidity typical for the outdoor Florida environment. *Tagetes patula* variety 'Little Devil Fire' was used as a comparison variety known to flower abundantly while maintaining a more compact habit under high night temperatures and high humidity.

In the Elburn, Ill. trial, a comparison of plant height, plant width, and number of inflorescences for 'Little Devil Fire' and 'Bonanza Yellow' is shown in Table 2. Data indicate that under these growth conditions, 'Little Devil Fire' is shorter and narrower than 'Bonanza Yellow'. While more compact, 'Little Devil Fire' has a similar number of inflorescences per plant as 'Bonanza Yellow'. As shown above in Table 1, *Tagetes patula* variety 'PAS1077390' has a compact habit similar to 'Little Devil Fire' and has fewer inflorescences per plant.

TABLE 2

Comparison of 'Little Devil Fire' and 'Bonanza Yellow' grown in Elburn, Illinois

| Characteristic | 'Little Devil Fire' | 'Bonanza Yellow' | Sample Size | t Critical $\alpha = .05$ | t Statistic | P Value |
| --- | --- | --- | --- | --- | --- | --- |
| Plant Height (cm) | 13.1 +/− 0.9 | 28.7 +/− 2.4 | 10 | 2.1 | −19.3 | 1.7E−13 |
| Plant Width (cm) | 19.2 +/− 1.5 | 37.5 +/− 3.5 | 10 | 2.1 | −15.2 | 9.9E−12 |
| Number Inflorescences | 17.7 +/− 1.8 | 19.6 +/− 3.1 | 10 | 2.1 | −1.7 | 0.1 |

In the Ruskin, Fla. trial, a comparison of plant height, plant width, and number of inflorescences of 'Little Devil Fire' and 'Bonanza Yellow' is shown in Table 3. Data indicates that under these growth conditions, 'Little Devil Fire' is shorter and narrower than 'Bonanza Yellow'. While maintaining a more compact habit, 'Little Devil Fire' has significantly more inflorescences per plant than 'Bonanza Yellow' under the high night temperatures and high humidity conditions.

TABLE 3

Comparison of 'Little Devil Fire' and 'Bonanza Yellow' grown in Ruskin, Florida

| Characteristic | 'Little Devil Fire' | 'Bonanza Yellow' | Sample Size | t Critical $\alpha = .05$ | t Statistic | P Value |
| --- | --- | --- | --- | --- | --- | --- |
| Plant Height (cm) | 27.7 +/− 3.8 | 48.6 +/− 3.6 | 10 | 2.1 | −12.7 | 2.0E−10 |
| Plant Width (cm) | 40.9 +/− 3.0 | 60.4 +/− 7.5 | 10 | 2.1 | −7.6 | 4.9E−07 |
| Number Inflorescences | 52.5 +/− 12.8 | 27.2 +/− 11.3 | 10 | 2.1 | 4.7 | 1.8E−04 |

In the Ruskin trial, a comparison of plant height, plant width, and number of inflorescences of *Tagetes patula* variety 'PAS1077390' to both 'Little Devil Fire' and 'Bonanza Yellow' is shown in Tables 4 and 5. Data indicates that *Tagetes patula* variety 'PAS1077390' maintains a compact habit similar to 'Little Devil Fire' and has significantly more inflorescences per plant than 'Bonanza Yellow' under the high night temperatures and high humidity conditions.

TABLE 4

Comparison of *Tagetes patula* variety 'PAS1077390' and 'Little Devil Fire' grown in Ruskin, Florida

| Characteristic | 'PAS1077390' | 'Little Devil Fire' | Sample Size | t Critical $\alpha = .05$ | t Statistic | P Value |
|---|---|---|---|---|---|---|
| Plant Height (cm) | 25.9 +/− 3.0 | 27.7 +/− 3.8 | 10 | 2.1 | 1.2 | 0.3 |
| Plant Width (cm) | 36.2 +/− 3.9 | 40.9 +/− 3.0 | 10 | 2.1 | 3.0 | 7.2E−03 |
| Number Inflorescences | 45.7 +/− 7.1 | 52.5 +/− 12.8 | 10 | 2.1 | 1.4 | 0.2 |

TABLE 5

Comparison of *Tagetes patula* variety 'PAS1077390' and 'Bonanza Yellow' grown in Ruskin, Florida

| Characteristic | 'PAS1077390' | 'Bonanza Yellow' | Sample Size | t Critical $\alpha = .05$ | t Statistic | P Value |
|---|---|---|---|---|---|---|
| Plant Height (cm) | 25.9 +/− 3.0 | 48.6 +/− 3.6 | 10 | 2.1 | 15.4 | 8.2E−12 |
| Plant Width (cm) | 36.2 +/− 3.9 | 60.4 +/− 7.5 | 10 | 2.1 | 9.0 | 4.2E−08 |
| Number Inflorescences | 45.7 +/− 7.1 | 27.2 +/− 11.3 | 10 | 2.1 | −4.4 | 3.6E−04 |

D. Breeding Marigold Plants

One aspect of the current invention concerns methods for producing seed of *Tagetes patula* variety 'PAS1077390'. In one embodiment of the invention, *Tagetes patula* variety 'PAS1077390' may be crossed with itself or with any second variety or plant to obtain progeny seeds. In a particular embodiment, the second plant may be a *Tagetes patula* plant and the progeny seed may be planted and grown to produce fertile hybrid progeny plants. A plant in accordance with the invention may be used in such crosses as the female plant or the male plant. In a further embodiment, *Tagetes patula* variety 'PAS1077390' may be used as a male parent plant and crossed with a *Tagetes erecta* plant as a female parent plant to obtain triploid (3N) marigold progeny seeds. Such seeds may be planted and grown to produce sterile triploid progeny plants. Methods such as those described herein may be used for propagation of *Tagetes patula* variety 'PAS1077390', or can be used to produce plants that are derived from *Tagetes patula* variety 'PAS1077390'. Plants derived from *Tagetes patula* variety 'PAS1077390' may be used, in certain embodiments, for the development of new marigold varieties such as described herein.

The development of new varieties using one or more starting varieties is well known in the art. In accordance with the invention, novel varieties may be created by crossing variety 'PAS1077390' followed by multiple generations of breeding according to such well known methods. New varieties may be created by crossing with any second plant. In selecting such a second plant to cross for the purpose of developing novel varieties, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are typically involved.

In one embodiment, progeny marigold plants of a backcross in which a plant described herein is the recurrent parent comprise (i) the desired trait from the non-recurrent parent and (ii) all of the physiological and morphological characteristics of marigold the recurrent parent as determined at the 5% significance level when grown in the same environmental conditions.

Backcrossing can be used to improve a variety, and may be used, for example, to introduce a desired allele or trait into the plant genetic background of any plant that is sexually compatible with a plant of the present invention. Backcrossing transfers a specific desired trait from one inbred or non-inbred source to a variety that lacks that trait. This can be accomplished, for example, by first crossing a variety of a desired genetic background (recurrent parent) to a donor inbred (non-recurrent parent), which carries the appropriate allele or loci for the desired trait(s) in question. The progeny of this cross are then mated back to the recurrent parent, followed by selection in the resultant progeny for the desired trait to be transferred from the non-recurrent parent. The process is repeated, for example for five or more backcross generations with selection for the desired trait, until a plant is obtained wherein essentially all of the desired morphological and physiological characteristics of the recurrent parent are recovered in the converted plant, in addition to the single transferred locus from the nonrecurrent parent. The progeny thus have the characteristic being transferred, but are like the superior parent for most or almost all other loci. The last backcross generation can be selfed to give true-breeding progeny when the trait being transferred is introgressed into a true-breeding variety.

The recurrent parent therefore provides the desired genetic background, while the choice of the particular nonrecurrent parent will depend on the purpose of the backcross. One of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele or an additive allele (between recessive and dominant) may also be transferred. In this instance it may be necessary to introduce a test of the progeny to determine if the desired characteristic has been successfully transferred.

Modified backcrossing may also be used with plants of the present invention. This technique uses different recurrent parents during the backcrossing. Modified backcrossing may be used to replace the original recurrent parent with a variety having certain more desirable characteristics or multiple parents may be used to obtain different desirable characteristics from each.

The plants of the present invention are particularly well suited for the development of new lines based on the genetic background of the plants. In selecting a second plant to cross with *Tagetes patula* variety 'PAS1077390' for the purpose of developing novel marigold varieties or lines, it will typically be preferred to choose those plants which either themselves exhibit one or more selected desirable characteristics or which exhibit the desired characteristic(s) when in hybrid combination. Examples of desirable traits may include, in specific embodiments, high flower yield, flower quality, high seed germination, seedling vigor, disease tolerance or resistance, and adaptability for soil and climate conditions such as drought or heat. Consumer-driven traits, such as a flower color, shape, and texture, are other examples of traits that may be incorporated into new lines of marigold plants developed by this invention.

E. Further Embodiments of the Invention

In other embodiments, the invention provides methods of vegetatively propagating a plant of the present invention. Such a method may comprise the steps of: comprising the steps of: (a) collecting tissue capable of being propagated from said plant; (b) cultivating said tissue to obtain proliferated shoots; and (c) rooting said proliferated shoots to obtain rooted plantlets. In other embodiments, such a method may further comprise growing *Tagetes* plants from the rooted plantlets. In still further embodiments, a plant of the invention is propagated by seed, wherein a plant may be used as either a female or a male parent for producing progeny seed and plants.

Also provided are methods of producing a *Tagetes* plant of the present invention, said method comprising introgressing a desired allele from a plant comprising the allele into a plant of a different genotype. In certain embodiments, such an allele may be inherited from or introgressed into *Tagetes* variety 'PAS1077390' or a progeny of any generation thereof comprising the allele.

Many single locus traits have been identified that are not regularly selected for in the development of a new inbred but that can be improved by backcrossing techniques. Single locus traits may or may not be transgenic; examples of these traits include, but are not limited to, resistance to bacterial, fungal, or viral disease, or herbicide or insect resistance. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of marigold plants for breeding is not necessarily dependent on the phenotype of a plant and instead can be based on genetic investigations. Thus, in one embodiment, the invention provides the genetic complement of a marigold plant as described herein. "Genetic complement" as used herein refers to the aggregate of nucleotide sequences, the expression of which sequences defines the phenotype of, in the present case, a marigold plant, or a cell or tissue of that plant. A genetic complement thus represents the genetic makeup of a cell, tissue or plant, and a hybrid genetic complement represents the genetic make up of a hybrid cell, tissue or plant. The genetic complement of variety 'PAS1077390' may be identified by any of the many well-known techniques in the art. For example, one can utilize a suitable genetic marker that is closely genetically linked to a trait of interest. One of these markers can be used to identify the presence or absence of a trait in the offspring of a particular cross, and can be used in selection of progeny for continued breeding. This technique is commonly referred to as marker assisted selection.

Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiology*, 147: 969-977), for example, and elsewhere, provides a mechanism for integrating single or multiple traits or QTL into a line. This molecular breeding-facilitated movement of a trait or traits into a line or variety may encompass incorporation of a particular genomic fragment associated with a particular trait of interest into the line or variety by the mechanism of identification of the integrated genomic fragment with the use of flanking or associated marker assays. In the embodiment represented here, one, two, three or four genomic loci, for example, may be integrated into a line via this methodology. When this line containing the additional loci is further crossed with another parental line to produce hybrid offspring, it is possible to then incorporate at least eight separate additional loci into the hybrid. These additional loci may confer, for example, such traits as disease resistance, drought or heat tolerance, or a flower quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

F. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio-Technology*, 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *BioTechnology*, 3:629-635, 1985; U.S. Pat. No. 5,563, 055).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994), and Ellul et al. (*Theor. Appl. Genet.*, 107:462-469, 2003).

A number of promoters have utility for plant gene expression for any gene of interest including but not limited to selectable markers, scoreable markers, genes for pest tolerance, disease resistance, or any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including in monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S); 1 the nopaline synthase promoter (An et al., *Plant Physiol.*, 88:547, 1988); the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a commelina yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO J.*, 4:2723, 1985), (3) hormones, such as abscisic acid (Marcotte et al., *Plant Cell*, 1:969, 1989), (4) wounding (e.g., wunl, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a marigold plant according to the invention. Non-limiting examples of particular genes and corresponding phenotypes one may choose to introduce into a marigold plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech Gen Engin Rev*, 9:207, 1991). The RNA could also be a catalytic RNA molecule (i.e., a ribozyme) engineered to cleave a desired endogenous mRNA product (see for example, Gibson et al., *Mol Biotech*, 7:125, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules that can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marigold Plant: As used herein, a marigold plant refers to any plant from the genus *Tagetes*, which may include but is not limited to *Tagetes patula*, *Tagetes erecta*, *Tagetes lucida*, *Tagetes minuta*, *Tagetes tenuifolia*, *Tagetes argentina*, *Tagetes biflora*, *Tagetes campanulata*, *Tagetes dianthiflora*, *Tagetes elliptica*, *Tagetes, filifolia*, *Tagetes Foetidissima*, *Tagetes heterocarpha*, *Tagetes hartwegii*, *Tagetes laxa*, *Tagetes Lemmoni*, *Tagetes micrantha*, and the like.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Plant Part: As used herein, a plant part refers to a part of a plant of the present invention. A plant part may be defined as comprising a cell of such plant, such as a cutting, a leaf, a floret, an ovule, pollen, a cell, a seed, a flower, an embryo, a meristem, a cotyledon, an anther, a root, a root tip, a pistil, a stem, and a protoplast or callus derived therefrom.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product.

Regeneration: The development of a plant from tissue culture.

Royal Horticultural Society (RHS) Colour Chart value: The RHS Colour Chart is a standardized reference which allows accurate identification of any color. A color's designation on the chart describes its hue, brightness and saturation. A color is precisely named by the RHS color chart by identifying the group name, sheet number and letter, e.g., Yellow-Orange Group 19A or Red Group 41B.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a marigold variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tissue Culture: A composition comprising isolated cells of the same or a different type or a collection of such cells organized into parts of a plant.

Transgene: A genetic locus comprising a sequence which has been introduced into the genome of a marigold plant by transformation.

H. Deposit Information

Deposits of at least 2500 seeds of *Tagetes patula* varieties 'PAS1077390' and 'Little Devil Fire', disclosed above and recited in the claims, have been made with the American Type Culture Collection (ATCC), 10801 University Blvd., Manassas, Va. 20110-2209. The dates of deposit were Feb. 2, 2016 and Feb. 2, 2016, respectively. The accession numbers for those deposited seeds of *Tagetes patula* varieties 'PAS1077390' and 'Little Devil Fire' are ATCC Accession No. PTA-122806 and ATCC Accession No. PTA-122805, respectively. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A seed of *Tagetes patula* variety 'PAS1077390', a sample of seed of said variety having been deposited under ATCC Accession Number PTA-122806.

2. A plant of *Tagetes patula* variety 'PAS1077390', a sample of seed of said variety having been deposited under ATCC Accession Number PTA-122806.

3. A plant part of the plant of claim 2.

4. The plant part of claim 3, wherein said part is selected from the group consisting of a flower, a floret, a cutting, a leaf, an ovule, pollen, or a cell.

5. A *Tagetes patula* plant, or a part thereof, having all the physiological and morphological characteristics of the plant of claim 2.

6. A tissue culture of regenerable cells of *Tagetes patula* variety 'PAS1077390', a sample of seed of said variety having been deposited under ATCC Accession Number PTA-122806.

7. The tissue culture according to claim 6, comprising cells or protoplasts from a plant part selected from the group consisting of embryos, meristems, cotyledons, pollen, leaves, anthers, roots, root tips, pistils, flowers, florets, seeds, and stems.

8. A plant regenerated from the tissue culture of claim 6, wherein the regenerated plant expresses all of the physiological and morphological characteristics of *Tagetes patula* variety 'PAS1077390', a sample of seed of said variety having been deposited under ATCC Accession Number PTA-122806.

9. A method of producing *Tagetes* seed, comprising crossing the plant of claim 2 with itself or a second marigold plant and collecting resulting seed.

10. The method of claim 9, wherein said second marigold plant comprises a plant of *Tagetes patula* variety 'Little Devil Fire', a sample of seed of which has been deposited under ATCC Accession Number PTA-122805.

11. The method of claim 10, further comprising backcrossing a progeny resulting from said crossing, wherein *Tagetes patula* variety 'Little Devil Fire' is used as the recurrent parent.

12. The method of claim 11, further comprising selecting a *Tagetes patula* variety resulting from said backcrossing.

13. The method of claim 9, wherein said second marigold plant is a *Tagetes erecta* plant and said *Tagetes* seed produces sterile triploid plants.

14. An F1 hybrid seed produced by the method of claim 9.

15. An F1 hybrid plant produced by growing the seed of claim 14.

16. A method for producing a seed of a variety 'PAS1077390'-derived *Tagetes patula* plant comprising the steps of:
　(a) crossing a *Tagetes patula* plant of variety 'PAS1077390' with a second marigold plant, a sample of seed of said variety 'PAS1077390' having been deposited under ATCC Accession Number PTA-122806; and
　(b) allowing seed of a 'PAS1077390'-derived *Tagetes patula* plant to form.

17. The method of claim 16, further comprising the steps of:
　(c) crossing a plant grown from said 'PAS1077390'-derived *Tagetes patula* seed with itself or a second marigold plant to yield additional 'PAS1077390'-derived seed;
　(d) growing said additional 'PAS1077390'-derived seed of step (c) to yield additional 'PAS1077390'-derived plants; and
　(e) repeating the crossing and growing steps of (c) and (d) to generate further 'PAS1077390'-derived plants.

18. A method of introducing a desired trait into *Tagetes patula* variety 'PAS1077390' comprising:
　(a) crossing a plant of variety 'PAS1077390' with a second marigold plant that comprises a desired trait to produce F1 progeny, a sample of seed of said variety 'PAS1077390' having been deposited under ATCC Accession Number PTA-122806;
　(b) selecting an F1 progeny that comprises the desired trait;
　(c) crossing the selected F1 progeny with a plant of variety 'PAS1077390' to produce backcross progeny;
　(d) selecting backcross progeny comprising the desired trait and the physiological and morphological characteristic of variety 'PAS1077390'; and
　(e) repeating steps (c) and (d) three or more times to produce selected fourth or higher backcross progeny that comprise the desired trait and otherwise all of the physiological and morphological characteristics of *Tagetes patula* variety 'PAS1077390' when grown in the same environmental conditions.

19. A plant comprising a desired trait produced by the method of claim 18.

20. A method of producing a plant of *Tagetes patula* variety 'PAS1077390' comprising an added desired trait, the method comprising introducing a transgene conferring the desired trait into a plant of *Tagetes patula* variety 'PAS1077390', a sample of seed of said variety 'PAS1077390' having been deposited under ATCC Accession Number PTA-122806.

21. A seed of the plant of claim 19.

22. A method of producing a *Tagetes patula* plant variety comprising the steps of:
　(a) crossing a plant of *Tagetes patula* variety 'Little Devil Fire' with a second *Tagetes patula* plant to produce progeny; and
　(b) backcrossing for at least about 1 to 7 subsequent generations a plant of *Tagetes patula* variety 'Little Devil Fire' to said progeny;
　　wherein said backcrossing comprises selecting a progeny plant comprising the traits of *Tagetes patula* plant variety 'PAS1077390'; and wherein samples of seed of said varieties 'PAS1077390' and 'Little Devil Fire' have been deposited under ATCC Accession Numbers PTA-122806 and PTA-122805, respectively.

* * * * *